Figure 1:
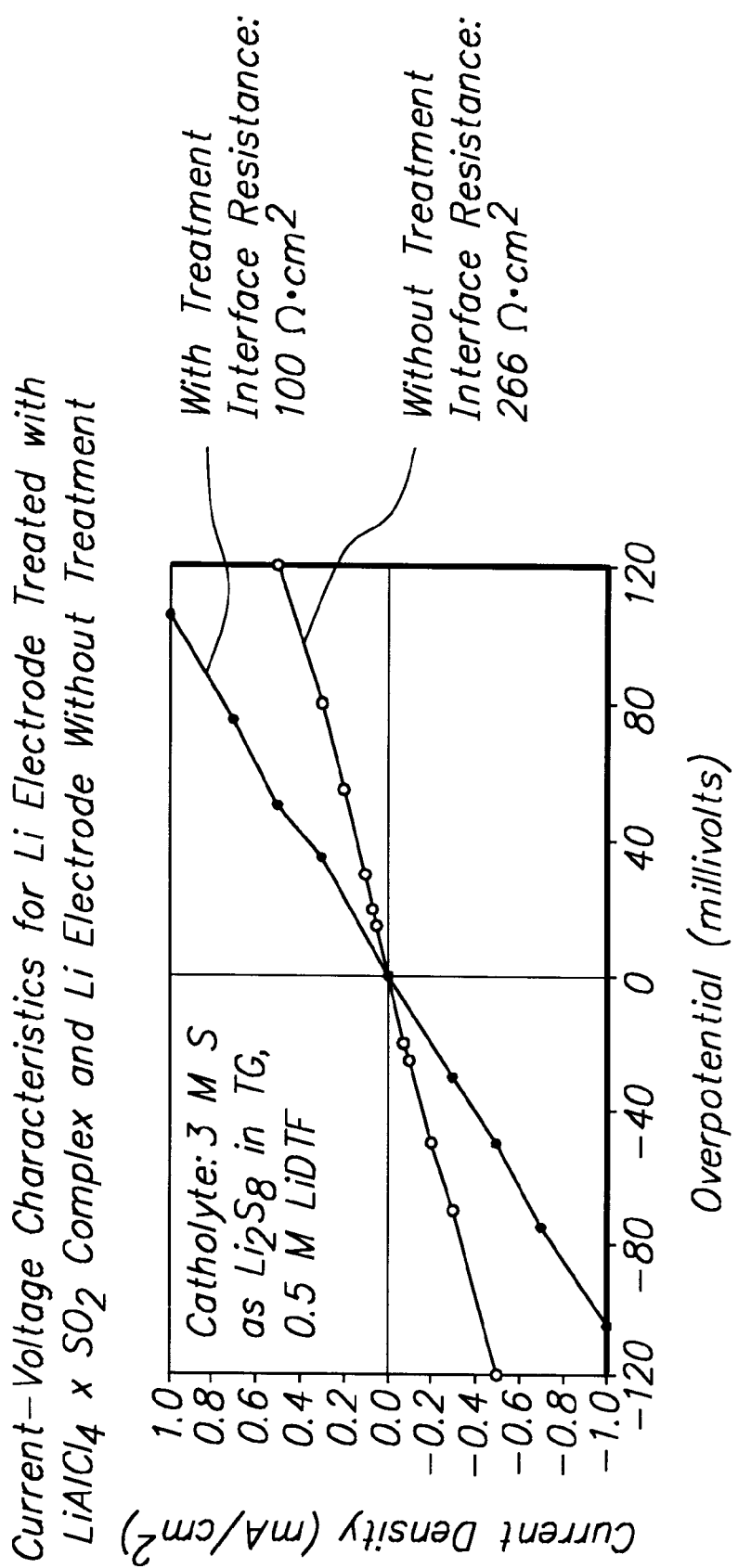

United States Patent
Nimon et al.

[11] Patent Number: 6,017,651
[45] Date of Patent: Jan. 25, 2000

[54] METHODS AND REAGENTS FOR ENHANCING THE CYCLING EFFICIENCY OF LITHIUM POLYMER BATTERIES

[75] Inventors: Yevgeniy S. Nimon, Walnut Creek; May-Ying Chu, Oakland; Steven J. Visco, Berkeley, all of Calif.

[73] Assignee: PolyPlus Battery Company, Inc., Berkeley, Calif.

[21] Appl. No.: 09/148,024

[22] Filed: Sep. 3, 1998

Related U.S. Application Data

[63] Continuation-in-part of application No. 08/948,892, Oct. 10, 1997, Pat. No. 5,814,420, which is a continuation-in-part of application No. 08/686,609, Jul. 26, 1996, Pat. No. 5,686,201, which is a continuation-in-part of application No. 08/479,687, Jun. 7, 1995, Pat. No. 5,582,623, which is a continuation of application No. 08/344,384, Nov. 23, 1994, Pat. No. 5,523,179.

[51] Int. Cl.[7] ................................................. H01M 4/36
[52] U.S. Cl. ................ 429/101; 429/105; 429/231.9; 429/231.95; 429/303; 429/314; 429/319
[58] Field of Search ................. 429/319, 231.9, 429/231.95, 314, 303, 101, 104, 105, 48, 338

[56] References Cited

U.S. PATENT DOCUMENTS

| | | | |
|---|---|---|---|
| 3,404,035 | 10/1968 | Kummer et al. | 136/6 |
| 3,413,150 | 11/1968 | Kummer et al. | 136/6 |
| 3,532,543 | 10/1970 | Nole et al. | 136/6 |
| 3,907,591 | 9/1975 | Lauck | 136/6 |
| 3,915,743 | 10/1975 | Lauck | 136/6 |
| 3,953,231 | 4/1976 | Farrington et al. | 136/6 |
| 4,143,214 | 3/1979 | Chang | 429/112 |
| 4,154,902 | 5/1979 | Schwartz | 429/105 |
| 4,218,523 | 8/1980 | Kalnoki-Kis | 429/101 |
| 4,268,587 | 5/1981 | Farrington et al. | 429/193 |
| 4,331,743 | 5/1982 | Dey et al. | 429/50 |
| 4,410,609 | 10/1983 | Peled et al. | 429/105 |
| 4,469,761 | 9/1984 | Bennett et al. | 429/50 |
| 4,644,911 | 2/1987 | Perichaud et al. | 429/194 |
| 4,780,380 | 10/1988 | Prafer | 429/201 |
| 4,833,048 | 5/1989 | Dejonghe et al. | 429/104 |
| 4,869,977 | 9/1989 | Connolly et al. | 429/101 |
| 4,917,974 | 4/1990 | De Jonghe et al. | 429/104 |
| 5,162,175 | 11/1992 | Visco et al. | 429/192 |
| 5,512,386 | 4/1996 | Simon | 429/105 |
| 5,523,179 | 6/1996 | Chu | 429/104 |
| 5,529,860 | 6/1996 | Skotheim et al. | 429/213 |
| 5,532,077 | 7/1996 | Chu | 429/102 |
| 5,582,623 | 12/1996 | Chu | 29/623.1 |
| 5,686,201 | 11/1997 | Chu | 429/52 |

FOREIGN PATENT DOCUMENTS

| | | |
|---|---|---|
| 0602984A2 | 6/1994 | European Pat. Off. . |
| 6-275313 | 9/1994 | Japan . |
| 2 273 603 | 10/1984 | United Kingdom . |
| 2 137406 | 6/1994 | United Kingdom . |

OTHER PUBLICATIONS

Abstract of proceedings of the 6th International Symposium on Power Sources 2, 1968, Brighton, Sussex, UK, Sep. 24–26, 1968, no month available.

(List continued on next page.)

*Primary Examiner*—Bruce F. Bell
*Attorney, Agent, or Firm*—Beyer & Weaver, LLP

[57] ABSTRACT

Batteries including a lithium electrode and a sulfur counter electrode that demonstrate improved cycling efficiencies are described. In one embodiment, an electrochemical cell having a lithium electrode and a sulfur electrode including at least one of elemental sulfur, lithium sulfide, and a lithium polysulfide is provided. The lithium electrode includes a surface coating that is effective to increase the cycling efficiency of said electrochemical cell. In a more particular embodiment, the lithium electrode is in an electrolyte solution, and, more particularly, an electrolyte solution including either elemental sulfur, a sulfide, or a polysulfide. In another embodiment, the coating is formed after the lithium electrode is contacted with the electrolyte. In a more particular embodiment, the coating is formed by a reaction between the lithium metal of the lithium electrode and a chemical species present in the electrolyte.

26 Claims, 3 Drawing Sheets

OTHER PUBLICATIONS

Coleman et al., "The Sulfur Electrode" proceedings of the 6th International Symposium on Power Sources, pp. 289–302 (1968).

Visco, S.J., Liu, M., Armand, B. and De Jonghe, L.C., Solid Redox Polymerization Electrodes and Their use in All–Solid–State Batteries, Mol. Cryst. Liq. Cryst., 190, p. 198, 1990, no month available.

Societe des Accumulateurs Fixes et de Traction, "Lithium–sulfur battery" Abstracts 111055d, Chemical Abstracts 66: 10360; 1967, no month available.

DeGott, P., "Polymere Carbone–Soufre Synthese Et Proprietes Electrochimiques," Doctoral Thesis as l'Institut National Polytechnique de Grenoble, (Date of Defense Jun. 19, 1986).

Lauck, H., "Storage battery with lithium anode and sulfur cathode," Abstract #9855s, Chemical Abstracts, 80:467–468; 1974, no month available.

Peled et al., Rechargeable Lithium–Sulfur Battery (Extended Abstact), Journal of Power Source, 26: 269–271, 1989, no month available.

Peled et al.; "Lithium–Sulfur Battery: Evaluation of Dioxolane–Based Electrolytes", J. Electrochem., Soc., 136(6): 1621–1624, Jun. 1989.

Peramunage and Licht, "A Solid Sulfur Cathode for Aqueous Batteries"; Science 261: 1029–1032, Aug. 20, 1993.

Rauh et al., "Formation of Lithium Polysulfides in Aprotic Media", J. Inorg., Nuc. Chem., 39: 1761–1765, 1977, no month available.

Rauh et al. "A Lithium/Dissolved Sulfur Battery with an Organic Electrolyte"; J. Electrochem. Soc., 126(4): 523–527, Apr. 1979.

Yamin and Peled, "Electrochemistry of Nonaqueous Lithium/Sulfur Cell", J. Power Sources, 9: 281–287, 1983, no month available.

Yamin et al., Lithium Sulfur Battery,: J. Electrochem. Soc., 135(5): 1045–1048, May 1988.

S.J. Visco, M.M. Doeff, and L.C. De Jonghe, "Thin–Film Technology for Solid–State Lithium Batteries Employing Solid Redox Poly–Merization Cathodes", pp. 89–92, Society of Vacuum Coaters, 1991, no month available.

Liu, Meilin, Visco, Steven J., and De Jonghe, Lutgard C., "Novel Solid Redox Polymerization Electrodes Electrochemical Properties", J. Electrochem Soc., vol. 138, No. 7, pp. 1896–1901, Jul 1991.

Liu, Meilin, Visco, Steven J., and De Jonghe, Lutgard C., "Novel Solid Redox Polymerization Electrodes All–Solid State, Thin–Film, Rechargeable Lithium Batteries", J. Electrochem Soc., vol. 138, No. 7, pp. 1891–1895, Jul. 1991.

Ue, Makoto, Visco, Steven J., and De Jonghe, Lutgard C., "Compariso of Cathode Utilization between Polymeric Organodisulfide and Titanium Disulfide in Solid Polymer Electrode Rechargeable Lithium Cells", Denki Kagaku, vol. 61, No. 12, pp. 1409–1415, 1993, no month available.

Meilin, Lui, "Novel Electrodes for Advanced Energy Storage System" Dissertation for Ph.D. at the University of Berkeley, Chapter 2, pp. 3–6, 1989, no month available.

J.R. Coleman, et al., "The Sulfur Electrode", (1968) 289–302, Defense Chemical Biological and Radiation Establishment, Defense Research Board, Ottawa, Canada, no month available.

R.D. Rauh et al., Rechargeability Studies of Ambient Temperature Lithium/Sulfur Batteries, EIC Corporation, 55 Chapel Street, Newton, MA 02158, no month available.

D. Nole, et al., "Battery Employing Lithium–Sulphur Electrodes with Non–Aqueous Electrolyte", U.S. Patent 3,532,543 (1970), no month available.

E. Peled, et al. "Lithium–Sulfur Battery: Evaluation of Dioxolane Based Electrodes", J. Electrochemical Society, 136, 1621–1624 (1989), no month available.

A. Yamin, et al. "Electrochemistry of a Nonaqueous Lithium/Sulfur Cell", J. Power Sources, 9, 281–287 (1983), no month available.

H. Yamin, et al. "Lithium Sulfur Battery—Oxidation/Reduction Mechanisms of Polysulfides in THF Solutions", J. Electrochemical Society,135, 1045–104 (1988), no month available.

S.B. Brummer, et al. "Low Temperature Lithium/Sulfur Secondary Battery", U.S. Energy Research and Development Administration Div. of Electric Energy Systems, 1–57 (1976), no month available.

E. Peled, et al. "Rechargeable Lithium–Sulfur Battery (Extended Abstract)", J. Power Sources, 26, 269–271 (1989), no month available.

Peled, et al. "Electrochemical Cell", U.S. Patent 4,410,609 (1983), no month available.

R.D. Rauh, et al. "Formation of Lithium Polysulfides in Aprotic Media", J. Inorg. Nuc. Chem., 39, 1761–1765 1977).

R.D. Rauh, et al. "A Lithium/Dissolved Sulfur Battery with an Organic Electrolyte", J. Electrochemical Society, 126, 523–527 91979), no month available.

R.D. Rauh, et al. "Rechargeability Studies of Ambient Temperature Lithium/Sulfur Batteries", 12th IECEC, 283–287 (1977).

A. Gavrilov, et al. "In Situ Morphological Study of Lithium–Electrolyte Interface", Electrochemical Society, (Extended Abstract), no month available.

Kavan, L., Novak, P., and Dousek, F.P., "Electrochimica Acto," vol. 33, No. 11, pp. 1605–1612, Mar. 8, 1988, Great Britain.

Brummer, S.B., et al., "Low Temperature Lithium/Sulfur Secondary Battery (Annual Progress Report, Dec. 1, 1974 – Dec. 1, 1975)," EIC Corporation, Apr. 1976, Newton, Massachusetts.

Larry A. Dominey, "Lithium Batteries" New Materials, Developments and Perspectives, 1994, New York, Industrial Chemistry Library, vol. 5, pp. 137–165, no month available.

Ronald Snaith, et al., "Lithium Chemistry" A Theoretical and Experimental Overview, 1995, New York, John Wiley & Sons, Inc., pp. 227–477, No month available.

METHODS AND REAGENTS FOR ENHANCING THE CYCLING EFFICIENCY OF LITHIUM POLYMER BATTERIES

1 CROSS REFERENCE TO RELATED U.S. PATENT APPLICATIONS

This application is a continuation-in-part of U.S. patent application Ser. No. 08/948,892 entitled Rechargeable Positive Electrodes, filed Oct. 10, 1997 (now U.S. Pat. No. 5,814,420, issued Sep. 29, 1998); which is a continuation-in-part of U.S. patent application Ser. No. 08/686,609 entitled Rechargeable Positive Electrodes, filed Jul. 26, 1996 (now U.S. Pat. No. 5,686,201, issued Nov. 11, 1997); which is a continuation-in-part of U.S. patent application Ser. No. 08/479,687 entitled Methods of Fabricating Rechargeable Positive Electrodes, filed Jun. 7, 1995 (now U.S. Pat. No. 5,582,623, issued Dec. 10, 1996); which is a continuation of U.S. patent application Ser. No. 08/344,384 entitled Rechargeable Positive Electrode, filed Nov. 23, 1994 (now U.S. Pat. No. 5,523,179, issued Jun. 4, 1996), each of which is incorporated herein by reference in its entirety for all purposes.

2 BACKGROUND OF THE INVENTION

2.1 Field of the Invention

The present invention relates to electrochemical batteries, and, more specifically, to lithium-metal batteries. More particularly, the present invention relates to methods and compositions that enhance the cycling efficiency of lithium-metal batteries, and, especially, lithium-active sulfur batteries. The present invention has applications in the fields of electrochemistry and battery technology.

2.2 The Related Art

Lithium battery technology continues to be an attractive option for providing light-weight, yet powerful energy sources. Lithium-sulfur secondary batteries are especially well suited to continuing market demands for more powerful and highly portable electronic devices. Examples of such batteries include those disclosed by De Jonghe, et al., in U.S. Pat. Nos. 4,833,048 and 4,917,974; and by Visco, et al., in U.S. Pat. No. 5,162,175. Nevertheless, the batteries described in these, and other references, have serious limitations (Rauh 1979; De Gott 1986). In particular, batteries using sulfur or polysulfide electrodes in combination with lithium, such as the $Li_2S_x$ batteries described by Peled and Yamin in U.S. Pat. No. 4,410,609, have suffered from poor cycling efficiencies (Rauh 1989).

Many of these difficulties are addressed by the batteries described in U.S. Pat. Nos. 5,523,179 and 5,532,077, both to Chu, each of which is incorporated herein by reference in its entirety and for all purposes. Briefly, the '179 and '077 patents describe solid-state batteries that comprise a lithium electrode in combination with an active sulfur-containing electrode. An "active sulfur" electrode is an electrode comprising elemental sulfur, or sulfur in an oxidation state such that the sulfur would be in its elemental state if the electrode was fully charged. The technology described in these patents is an important advance in lithium battery technology, in particular by describing batteries having large energy densities and good cycling performance.

Nevertheless, the challenge of providing improved batteries, and especially batteries having cycling efficiencies of better than 70%, remains. In particular, the cycling efficiency of lithium-sulfur batteries is limited by the slow degradation of the lithium electrode surface arising from the formation of dendritic and/or high surface area "mossy lithium"—lithium-sulfur complexes that are detached from the lithium electrode and float freely in the electrolyte. These phenomena prevent high cycling efficiencies by steadily degrading the lithium electrode surface over successive rechargings. To compensate for this loss, extra lithium must be provided for the lithium electrode increasing the cost and weight of the battery. The use of additional metals also increases the burden of disposing the battery as additional toxic materials must be processed. Mossy lithium can also present a fire hazard by creating fine particles of lithium metal that can ignite on contact with air.

Various attempts have been made to provide lithium batteries having high cycling efficiencies with some success. One type of lithium battery, commonly used for military applications, comprises a lithium-sulfur dioxide ($Li-SO_2$) battery to which $LiAlCl_4.3SO_2$ has been used as an inorganic electrolyte. The cycling efficiencies of such batteries have been demonstrated to be as high as 95% (Dey 1989; Dunger, 1993). However, $Li-SO_2$ batteries are not a viable alternative for the civilian commercial market. Thus, there remains a need for commercially viable batteries having high cycling efficiencies. The present invention meets these and other such needs.

3 SUMMARY OF THE INVENTION

The present invention provides batteries including a lithium electrode and a sulfur counter electrode that demonstrate improved cycling efficiencies. In one embodiment, the present invention includes an electrochemical cell having a lithium electrode and a sulfur electrode including at least one of elemental sulfur, lithium sulfide, and a lithium polysulfide. The lithium electrode includes a surface coating that is effective to increase the cycling efficiency of said electrochemical cell. In a more particular embodiment, the lithium electrode is in an electrolyte solution, and, more particularly, an electrolyte solution including either elemental sulfur, a sulfide, or a polysulfide.

In another embodiment, the lithium electrode is coated prior to contact with the electrolyte. In a more particular embodiment, the coating is formed by contacting the surface of the lithium electrode with $LiAlCl_4.3SO_4$. The coating can be a reaction product resulting from the contact of the lithium electrode surface with $LiAlCl_4.3SO_4$, e.g., $Li_2S_2O_4$.

In still another embodiment, the coating is formed after the lithium electrode is contacted with the electrolyte. In a more particular embodiment, the coating is formed by a reaction between the lithium metal of the lithium electrode and a chemical species present in the electrolyte. More particularly, the chemical species can include a multivalent transition- or alkaline earth metal. Still more particularly, the multivalent metal is selected from the group consisting of Mg, Al, Bi, Sn, Pb, Cd, Si, In, and Ga.

In yet another embodiment, the present invention provides an electrochemical cell that comprises an electrode and an electrolyte containing one or more sulfur compounds including at least one of elemental sulfur, sulfides, and polysulfides. The electrolyte further includes a reagent that is effective to form a substantially insoluble metal-sulfide complex in the electrolyte to increase thereby the cycling efficiency of said electrode. More particularly, the electrode is a lithium electrode. Still more particularly, the lithium electrode is combined with a sulfur electrode. The sulfur electrode can include at least one of elemental sulfur, sulfides, and polysulfides. The sulfur electrode can further include an ionically conductive material, such as a polyalkyleneoxide. The reagent is, in more specific embodiments, a salt of barium (Ba) or molybdenum (Mo).

In another aspect, the present invention also provides an electrochemical cell that includes a lithium-tin alloy, the surface of which has a lithium oxide coating, and a sulfur electrode including at least one of elemental sulfur, a lithium sulfide, or a lithium polysulfide. The cell can further include an electrolyte that includes at least one of elemental sulfur, a sulfide, or a polysulfide.

These and other aspects and advantages will become apparent when the Description below is read in conjunction with the accompanying Drawings.

4 BRIEF DESCRIPTION OF THE DRAWINGS

FIG. 1 is a graph comparing the current density vs. overpotential of a lithium metal electrode treated with $LiAlCl_4.3SO_4$ against an untreated lithium metal electrode in an electrolyte comprising 3 M sulfur (in the form of $Li_2S_8$) in tetraglyme and 0.5 M lithium trifluoromethanesulfonimide (LiTFSI).

Figure 2:
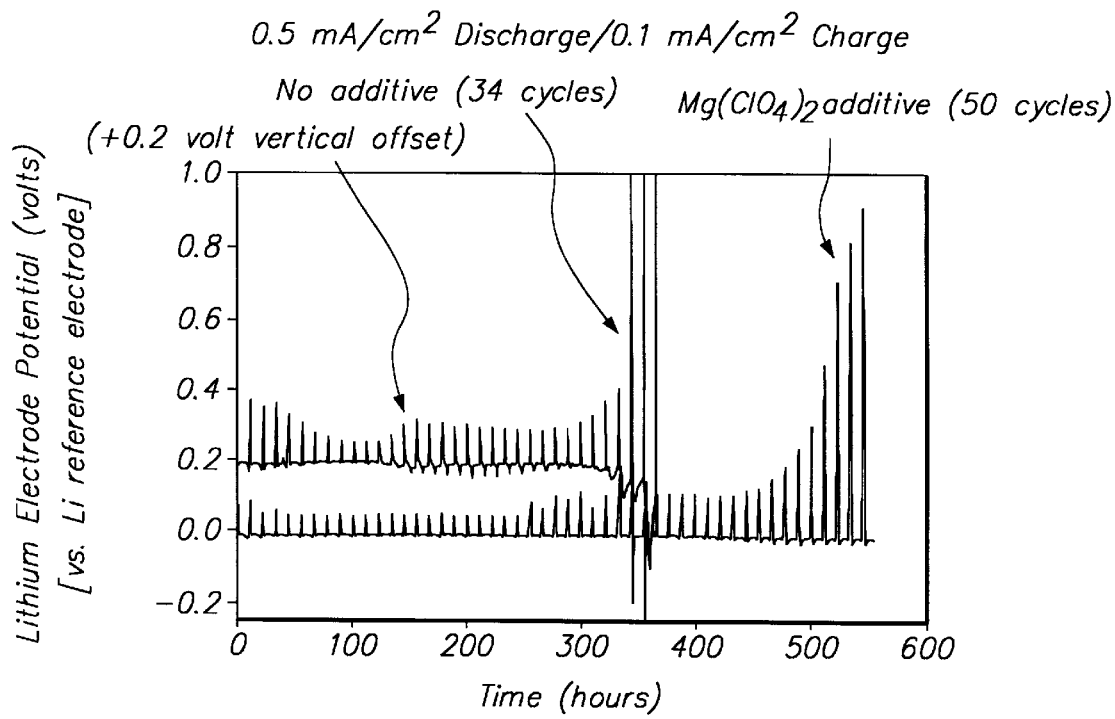

FIG. 2 is a graph comparing the lithium electrode potential (volts (V), Li reference) vs. time (hours) under a 0.5 $mA/cm^2$ discharge/0.1 $mAcm^2$ charge cycling regimen for a lithium metal electrode in an electrolyte comprising 3 M sulfur (in the form of $Li_2S_8$) in tetraglyme and 0.5 M lithium trifluoromethanesulfonimide (LiTFSI) with an additive of $Mg(ClO_4)_2$ (black trace) and without such additive (gray trace). Note the lithium electrode potential without the additive is offset vertically (+0.1 V) to enhance legibility of the two traces. Both traces are to scale.

Figure 3:
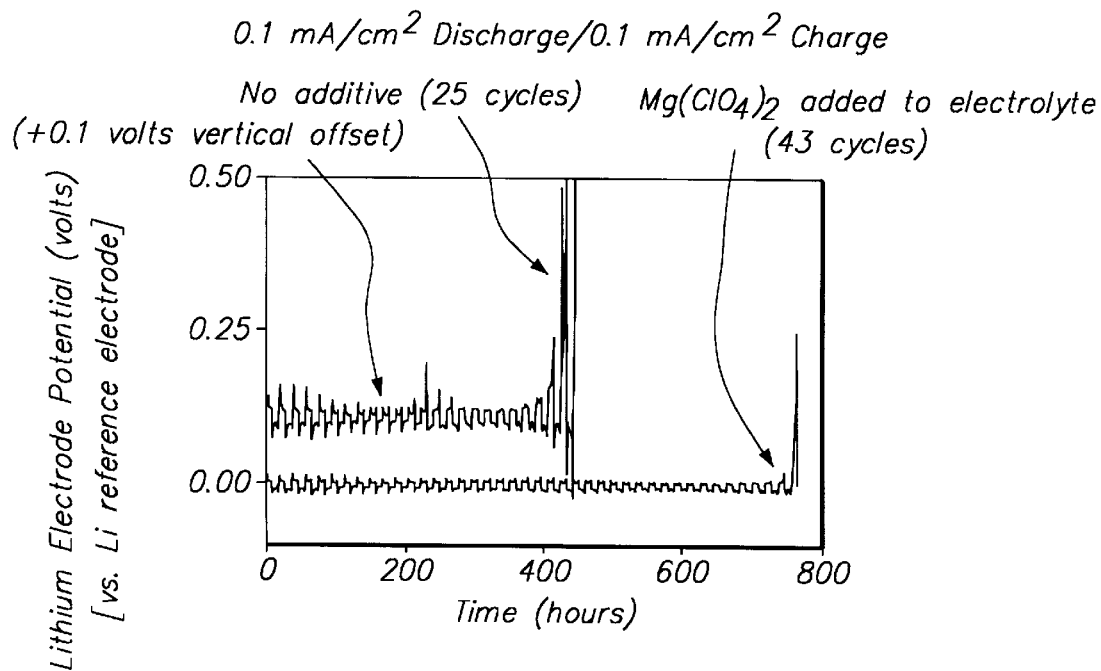

FIG. 3 is a graph comparing the lithium electrode potential (volts (V), Li reference) time (hours) under a 0.1 $mA/cm^2$ discharge/0.1 $mAcm^2$ charge cycling regimen for a lithium metal electrode in an electrolyte comprising 3 M sulfur (in the form of $Li_2S_8$) in tetraglyme and 0.5 M lithium trifluoromethanesulfonimide (LiTFSI) with an additive of $Mg(ClO_4)_2$ (black trace) and without such additive(gray trace). Note the lithium electrode potential without the additive is offset vertically (+0.1 V) to enhance legibility of the two traces. Both traces are to scale.

Figure 4:
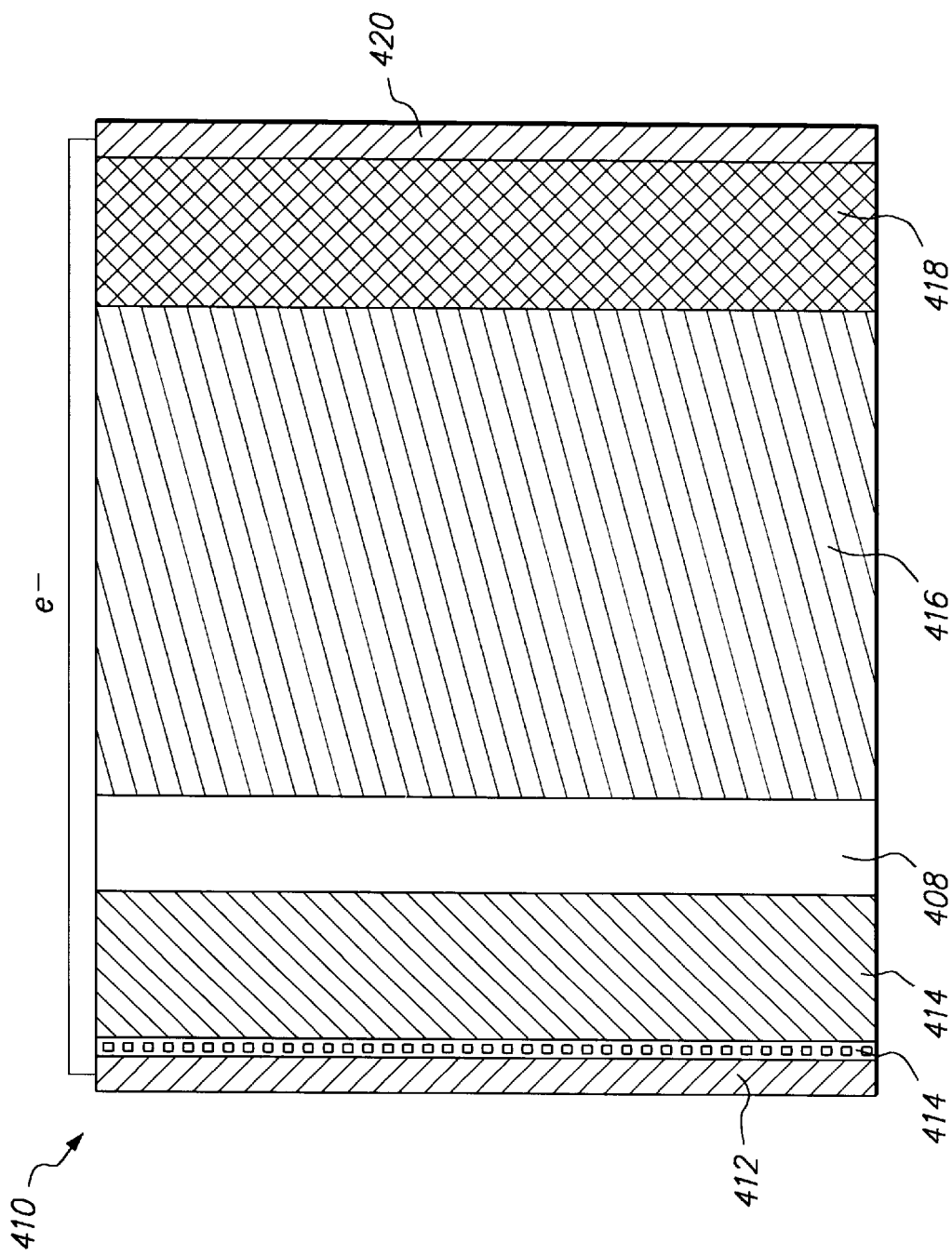

FIG. 4 is a schematic figure of a battery in accordance with one embodiment of the invention.

5 DESCRIPTION OF SOME EMBODIMENTS OF THE INVENTION

5.1 Overview

The present invention provides methods and reagents for making and using lithium batteries aving improved cycling efficiency compared to current lithium polymer batteries available in the general commercial market. More particularly, the methods and reagents provided herein include agents that modify the lithium electrode surface to increase the cycling efficiency of electrochemical cells using such electrodes. Without wishing to be bound by any particular theory of action, it is believed that the methods and reagents described herein act to reduce and/or prevent dendrite and mossy lithium formation to preserve thereby the lithium metal electrode. These methods and reagents include electrode coatings (Sections 5.2 and 5.3.1), agents that form insoluble sulfides (Section 5.3.2), and amorphous tin composite oxide (ATCO) materials as discovered by Fujifilm Celltec (Idota 1997), and active/inactive composites (Dahn 1998) (alloying phase/conductive phase) such as $Sn_2Fe/SnFe_3C$ and the lithium-copper-tin system reported by Thackeray, $Li_2CuSn/Cu_6Sn_5$ (Thackeray 1998) (Section 5.4). These methods and reagents provide lithium batteries having improved cycling efficiency, increased shelf-life, and reduced voltage delay after initiation of battery discharge.

Thus, in a general aspect, the present invention provides an electrochemical cell having a lithium metal electrode having a surface coating that is effective to increase the cycling efficiency of the electrochemical cell. In a more particular aspect, the electrochemical cell includes an electrolyte solution, and, still more particularly, a polysulfide-containing electrolyte solution. Several embodiments of the invention are presented below.

5.2 Lithium Electrodes Coated with $LiAlCl_4.3SO_2$

In a first aspect, the present invention includes methods and reagents for making lithium batteries in which the lithium electrode of the battery includes a surface coating that is formed by contacting the surface of the lithium electrode with $LiAlCl_4.3SO_2$ prior to contact between the electrode and electrolyte. In a more particular embodiment, the electrode coating is a product of a chemical reaction between the lithium metal of the electrode surface and the $LiAlCl_4.3SO_2$ reagent. In a still more specific embodiment, the coating on the electrode comprises $Li_2S_2O_4$.

The electrode can be coated using ordinary methods and materials known to those of skill in the electrochemical or metallurgical arts. The $LiAlCl_4.3SO_2$ reagent used to coat the electrode can be made using the procedures described in literature procedures in which $SO_2$ is bubbled into a mixture of stoichiometric amounts of lithium chloride (LiCl) and aluminum chloride ($AlCl_3$) until a straw-colored liquid forms (Foster 1988). In one embodiment, the $LiAlCl_4.3SO_2$ is applied as a liquid on the surface of the electrode using brush, edge, roller, spray, or the like to a surface density of less than about 10 $\mu l/cm^2$, more particularly less than about 5 $\mu l/cm^2$, and still more particularly between about 1 $\mu l/cm^2$ and about 3 $\mu l/cm^2$. In one embodiment, the surface density of the coating is about 2 $\mu l/cm^2$. The application is performed under appropriate safety conditions, such as in a glove box under an inert atmosphere (e.g., an argon (Ar) atmosphere) at ambient temperature and pressure. The electrode is then allowed to cure at a time and temperature suitable to provide a coating having suitable mechanical properties. For example, a coatings having desirable properties have been prepared by applying $LiAlCl_4.3SO_2$ at a density of about 2 $\mu l/cm^2$ and curing the coated metal a temperatures between about 25° C. and about 30° C. for between about 35 minutes and about 45 minutes.

Batteries using lithium metal electrodes treated according to the present invention in polysulfide-containing counter electrodes have been found to have superior current-voltage characteristics compared with untreated lithium metal electrodes under the same conditions. As discussed in Section 6.1 below, the current-voltage characteristics of a cell having a lithium metal electrode treated with 2 $\mu l/cm^2$ of $LiAlCl_4.3SO_2$ as described above showed significantly lower interface resistance compared with a cell having an untreated electrode (100 ohm·$cm^2$ vs. 266 ohm·$cm^2$, see FIG. 1). This result indicates that lithium metal electrodes treated in accordance with the present invention have superior cycling efficiencies and energy delivery characteristics compared with lithium metal electrodes lacking such treatment.

5.3 Lithium-Sulfur Batteries Including Mossy-Lithium-Reducing Electrolyte Additives In another aspect, the present invention provides reagents that, when added to the electrolyte of the lithium electrode-containing electrochemical cell that includes a polysulfide-containing electrolyte, either provide an electrode coating effective to increase the cycling efficiency of the cell or produce insoluble sulfide salts that for insoluble complexes that increase the cycling efficiency of the electrochemical cell.

5.3.1 Lithium-Alloy Forming Additives

In one embodiment, the present invention provides electrochemical cells that include polysulfide-containing electrolytes to which salts of lithium-alloy forming multivalent metals have been added. Addition of salts of transition- or alkaline earth metals (Me) such as, but not limited to, Mg, Al, Bi, Sn, Pb, Cd, Si, In, Ga, to the electrolyte of lithium metal electrode/polysulfide-containing counter electrochemical cells provided superior performance to non-augmented cells. Typical concentrations of salts of above-mentioned Me salts that have been found to provide useful results range from about 0.01 moles/liter to about 0.5 moles/liter, more particularly, about 0.02 moles/liters to about 0.4 moles/liter, and, still more particularly, between about 0.03 moles/liter and about 0.3 moles/liter. Particularly good results were obtained at Me salt concentrations between about 0.05 to about 0.2 moles/liter. Those having skill in the electrochemistry arts will be able to determine still more salts using familiar resources, reagents, and methods.

The results of comparisons of lithium electrode potential (volts) as a function of time for galvanostatic cell cyclings performed with a 0.5 mA/cm$^2$ discharge/0.1 mA/cm$^2$ charge showed that cells having electrolytes containing the above-described additives had notably more cycles before lithium stripping compared to cells having non-augmented electrolytes. As described Section 6.2 and shown in FIG. 2, cells including 0.5 moles/liter Mg(ClO$_4$)$_2$ ran for 50 cycles before stripping as compared to non-augmented cells that ran for only 34 cycles before stripping (85% cycling efficiency vs. 77% cycling efficiency as computed using Formula (1)). Similarly, as discussed in Section 6.3 and shown in FIG. 3, when the same experiment was performed with a cycling of 0.1 mA/cm$^2$ discharge/0.mA/cm$^2$ charge, cells including 0.05 moles/liter Mg(ClO$_4$)$_2$ delivered 43 cycles compared to only 25 cycles for the control (82% cycling efficiency vs. 68% cycling efficiency as computed using Formula (1).

Without wishing to be bound by any theory, it is believed that addition of Me salts leads to an electrochemical deposition of these Me on the surface of Li and possibly the formation of thin layers of Li—Me alloys. On the surface of electrode Li is incorporated into the matrix and is thus protected from the reaction with strongly oxidizing polysulfides of the counter electrode. As a result, the plating of dendiritic lithium or loss of lithium to the electrolyte solution (e.g., as Li$_2$S$_8$) is suppressed or slowed.

5.3.2 Insoluble Sulfur Complex Forming Additives

In one embodiment, the present invention provides electrochemical cells that include polysulfide-containing electrolytes to which salts of multivalent metals capable of forming insoluble complexes with polysulfides that are effective to react with the electrode's surface to increase the battery's cycling efficiency have been added. In one embodiment, the electrode is a lithium electrode. In another embodiment, the lithium electrode is combined with a sulfur-containing electrode, and, more specifically, an active sulfur-containing electrode. In a more specific embodiment, the electrochemical cell of the invention includes lithium and active sulfur-containing electrodes in which the active sulfur-containing electrode includes a polyalkylene oxide, and, still more particularly, polyethylene oxide. In general, the choice of salt additive will depend on the chemical properties of the polysulfide to be complexed and the electrolyte. Those having skill in the electrochemistry arts will be familiar with the resources, reagents, and methods to determine useful salt additives.

In one experiment, discussed in Section 6.4, comparing cells augmented with 0.1 moles/liter Ba(ClO$_4$) to non-augmented cells, both discharged at 0.1 and 0.5 mA/cm$^2$ and charged at 0.1 mA/cm$^2$, it was found that augmented cells had a significantly higher lithium metal cycling efficiency (90% at 0.5 mA/cm$^2$ and 76% at 0.1 mA/cm$^2$ compared with 77% and 68% respectively for non-augmented cells as computed using Formula (1). Without wishing to be bound by theory, it is believed that polysulfide-containing electrolytes, and, more particularly, electrochemical cells in which a lithium metal electrode is combined with a polysulfide counter electrode, allow for the formation of lithium-polysulfide and/or lithium-sulfide complexes. In particular, it is believed that at least a portion of the lithium is lost from the electrode as Li$_2$S$_x$ (e.g., Li$_2$S$_8$). Thus, the addition of reagents that are effective to form metal-polysulfide and/or metal-sulfide complexes that have greater thermodynamic stability than lithium-sulfide complexes (e.g., BaS$_2$) will reduce the loss of lithium to the electrolyte and increase cycling efficiency. The formation of metal-sulfide complexes may also reduce the formation of surface dendrites; thereby imparting greater stability to the surface of the lithium metal electrode.

5.4 Lithium-Tin Oxide Electrodes

In another aspect, the present invention provides electrochemical cells that include an electrode that comprises a lithium-tin alloy including amorphous tin composite oxide (ATCO) materials, and active/inactive composites (alloying phase/conductive phase) such as Sn$_2$Fe/SnFe$_3$C or the lithium-copper-tin system Li$_2$CuSn/Cu$_6$Sn$_5$, and, more particularly, a lithium-tin alloy having surface coating that comprises lithium oxide (Li$_2$O). More specific embodiments include electrochemical cells in which the electrode just described is included with an electrolyte and a counter electrode, more particularly, an electrolyte that includes a polysulfide. In one embodiment, the electrode of this aspect of the invention is formed using the methods described in U.S. Pat. No. 5,618,640, which is incorporated herein in its entirety for all purposes.

Without wishing to be bound to any particular theory of action, it is believed that the combination of lithium metal with tin oxide will lead an irreversible reaction of lithium with the oxygen bound to the tin to provide a conductive lithium oxide matrix that holds therein dispersed tin clusters and lithium metal. A reversible alloying of lithium and tin can occur within the matrix to provide a lithium electrode which is resistant to the formation of mossy lithium.

5.5 Batteries

5.5.1 Battery Design

Batteries of this invention may be constructed according to various known processes for assembling cell components and cells. Generally, the invention finds application in any cell configuration. The exact structure will depend primarily upon the intended use of the battery unit. Examples include thin film with porous separator, thin film polymeric laminate, jelly roll (i.e., spirally wound), prismatic, coin cell, etc.

Generally, batteries employing the negative electrodes of this invention will be fabricated with a separate electrolyte that is distinct from the surface treatment layer. It is possible, however, that the surface layer could by itself serve as a solid state electrolyte. If a separate electrolyte is employed, it may be in the liquid, solid (e.g., polymer), or gel state. It may be fabricated together with the negative electrode as a unitary structure (e.g., as a laminate). Such unitary structures will most often employ a solid or gel phase electrolyte.

The negative electrode is spaced from the positive electrode, and both electrodes may be in material contact with an electrolyte separator. Current collectors contact both the positive and negative electrodes in a conventional manner and permit an electrical current to be drawn by an external circuit. In a typical cell, all of the components will be enclosed in an appropriate casing, plastic for example, with only the current collectors extending beyond the casing. Therefore, reactive elements, such as sodium or lithium in the negative electrode, as well as other cell elements are protected.

Referring now to FIG. 4, a cell 410 in accordance with a preferred embodiment of the present invention is shown. Cell 410 includes a negative current collector 412 which is formed of an electronically conductive material. The current collector serves to conduct electrons between a cell terminal (not shown) and a negative electrode 414 (such as lithium) to which current collector 412 is affixed. Negative electrode 414 is made from lithium or other similarly reactive material, and includes a surface layer 408 (e.g., barium sulfide) formed opposite current collector 412. Surface layer 408 of negative electrode 414 contacts an electrolyte in an electrolyte region 416. As mentioned, the electrolyte may be liquid, gel, or solid (e.g., a polymer). To simplify the discussion of FIG. 4, the electrolyte may sometimes be referred to as "liquid electrolyte." An example of a solid electrolyte is polyethylene oxide. An example of gel electrode is polyethylene oxide containing a significant quantity of entrained liquid such as an aprotic solvent.

A positive electrode 418 abuts the side of electrolyte region 416 opposite negative electrode 414. As electrolyte region 416 is an electronic insulator and an ionic conductor, positive electrode 418 is ionically coupled to but electronically insulated from negative electrode 414. Finally, the side of positive electrode 418 opposite electrolyte region 416 is affixed to a positive current collector 420. Current collector 420 provides an electronic connection between a positive cell terminal (not shown) and positive electrode 418.

Current collector 420 should resist degradation in the electrochemical environment of the cell and should remain substantially unchanged during discharge and charge. In one embodiment, the current collectors are sheets of conductive material such as aluminum or stainless steel. The positive electrode may be attached to the current collector by directly forming it on the current collector or by pressing a preformed electrode onto the current collector. Positive electrode mixtures formed directly onto current collectors preferably have good adhesion. Positive electrode films can also be cast or pressed onto expanded metal sheets. Alternately, metal leads can be attached to the positive electrode by crimp-sealing, metal spraying, sputtering or other techniques known to those skilled in the art. Some positive electrode can be pressed together with the electrolyte separator sandwiched between the electrodes. In order to provide good electrical conductivity between the positive electrode and a metal container, an electronically conductive matrix of, for example, carbon or aluminum powders or fibers or metal mesh may be used.

An optional inert separator in region 416 prevents electronic contact between the positive and negative electrodes. Such separators are commonly used in liquid electrolyte systems. A separator may occupy all or some part of electrolyte compartment 416. Preferably, it will be a highly porous/permeable material such as a felt, paper, or microporous plastic film. It should also resist attack by the electrolyte and other cell components under the potentials experienced within the cell. Examples of suitable separators include glass, plastic, ceramic, and porous membranes thereof among other separators known to those in the art. In one specific embodiment, the separator is CELGARD 2300 or CELGARD 2400 available from Celgard, LLC of Charlotte, N.C.

In an alternative embodiment, no separator is employed. The surface layer on the negative electrode prevents the positive and negative electrodes from contacting one another and serves the function of a separator. In such cases, the surface layer should be tough. It may be relatively thick and made from a material that resists cracking and abrasion.

In some embodiments of the invention, the cell may be characterized as a "thin film" or "thin layer" cell. Such cells possess relatively thin electrodes and electrolyte separators. Preferably, the positive electrode is no thicker than about 300 $\mu$m, more preferably no thicker than about 150 $\mu$m, and most preferably no thicker than about 100 $\mu$m. The negative electrode preferably is no thicker than about 100 $\mu$m and more preferably no thicker than about 100 $\mu$m. Finally, the electrolyte separator (when in a fully assembled cell) is no thicker than about 100 $\mu$m and more preferably no thicker than about 40 $\mu$m.

The present invention can be used with any of a number of battery systems employing a highly reactive negative electrode such as lithium or other alkali metal. For example, any positive electrode used with lithium metal or lithium ion batteries may be employed. These include lithium manganese oxide, lithium cobalt oxide, lithium nickel oxide, lithium vanadium oxide, etc. Mixed oxides of these compounds may also be employed such as lithium cobalt nickel oxide. As will be explained in more detail below, a preferred application of the electrodes of this invention is in lithium-sulfur batteries.

While the above examples are directed to rechargeable batteries, the invention may also find application in primary batteries. Examples of such primary batteries include lithium-manganese oxide batteries, lithium-$(CF)_x$ batteries, lithium sulfur dioxide batteries and lithium iodine batteries.

The surface layer allows one to use a reactive lithium metal electrode in a manner that resembles the use of lithium ion batteries. Lithium ion batteries were developed because they had a longer cycle life and better safety characteristics than metal lithium batteries. The relatively short cycle life of metallic lithium batteries has been due, in part, to the formation of dendrites and/or high surface area "mossy" lithium which can grow from the lithium electrode across the electrolyte and to the positive electrode where they short circuit the cells. Not only do these short circuits prematurely kill the cells, they pose a serious safety risk. The surface layer of this invention prevents formations of dendrites and/or mossy lithium and thereby improves the cycle life and safety of metallic lithium batteries. Further, the batteries of this invention will perform better than lithium ion batteries because they do not require a carbon intercalation matrix to support lithium ions. Because the carbon matrix does not provide a source of electrochemical energy, it simply represents unproductive weight that reduces a battery's energy density. Because the present invention does not employ a carbon intercalation matrix, it has a higher energy density than a conventional lithium ion cell—while providing better cycle life and safety than metallic lithium batteries studied to date. In addition, the lithium metal batteries of this invention do not have a large irreversible capacity loss associated with the "formation" of lithium ion batteries.

5.5.2 Lithium-Sulfur Batteries

Sulfur positive electrodes and metal-sulfur batteries are described in U.S. Pat. No. 5,686,201 issued to Chu on Nov.

11, 1997 and U.S. patent application Ser. No. 08/948,969 naming Chu et al. as inventors, filed on Oct. 10, 1997. Both of these documents are incorporated by reference for all purposes. The sulfur positive electrodes preferably include in their theoretically fully charged state sulfur and an electronically conductive material. At some state of discharge, the positive electrode will include one or more polysulfides and possibly sulfides, which are polysulfides and sulfides of the metal or metals found in the negative electrode. In some embodiments, the fully charged electrode may also include some amount of such sulfides and/or polysulfides.

The positive electrode is fabricated such that it permits electrons to easily move between the sulfur and the electronically conductive material, and permits ions to move between the electrolyte and the sulfur. Thus, high sulfur utilization is realized, even after many cycles. If the lithium-sulfur battery employs a solid or gel state electrolyte, the positive electrode should include an electronic conductor (e.g., carbon) and an ionic conductor (e.g., polyethylene oxide) in addition to the sulfur electroactive material. If the battery employs a liquid electrolyte, the positive electrode may require only an electronic conductor in addition to the sulfur electroactive material. The electrolyte itself permeates the electrode and acts as the ionic conductor. In the case of a liquid electrolyte cell, the battery design may assume two formats: (1) all active sulfur (elemental sulfur, polysulfides and sulfides of the positive electrode) is dissolved in electrolyte solution (one phase positive electrode) and (2) the active sulfur is distributed between a solid phase (sometimes precipitated) and a liquid phase.

When the metal-sulfur battery cells of this invention include a liquid electrolyte, that electrolyte should keep many or all of sulfur discharge products in solution and therefore available for electrochemical reaction. Thus, they preferably solubilize lithium sulfide and relatively low molecular weight polysulfides. In a particularly preferred embodiment, the electrolyte solvent has repeating ethoxy units ($CH_2CH_2O$). This may be a glyme or related compound. Such solvents are believed to strongly coordinate lithium and thereby increase the solubility of discharge products of lithium-sulfur batteries. Suitable liquid electrolyte solvents are described in more detail in U.S. patent application Ser. No. 08/948,969, previously incorporated by reference.

It should be understood that the electrolyte solvents of this invention may also include cosolvents. Examples of such additional cosolvents include sulfolane, dimethyl sulfone, dialkyl carbonates, tetrahydrofuran (THF), dioxolane, propylene carbonate (PC), ethylene carbonate (EC), dimethyl carbonate (DMC), butyrolactone, N-methylpyrrolidinone, dimethoxyethane (DME or glyme), hexamethylphosphoramide, pyridine, N,N-diethylacetamide, N,N-diethylformamide, dimethylsulfoxide, tetramethylurea, N,N-dimethylacetamide, N,N-dimethylformamide, tributylphosphate, trimethylphosphate, N,N,N',N'-tetraethylsulfamide, tetraethylenediamine, tetramethylpropylenediamine, pentamethyldiethylenetriamine, methanol, ethylene glycol, polyethylene glycol, nitromethane, trifluoroacetic acid, trifluoromethanesulfonic acid, sulfur dioxide, boron trifluoride, and combinations of such liquids.

The surface layers employed in this invention may allow the use of electrolyte solvents that work well with sulfides and polysulfides but may attack lithium. Examples of solvents in this category include amine solvents such as diethyl amine, ethylene diamine, tributyl amine, amides such as dimethyl acetamide and hexamethyl phosphoramide (HMPA), etc.

Exemplary but optional electrolyte salts for the battery cells incorporating the electrolyte solvents of this invention include, for example, lithium trifluoromethanesulfonimide ($LiN(CF_3SO_2)_2$), lithium triflate ($LiCF_3SO_3$), lithium perchlorate ($LiClO_4$), $LiPF_6$, $LiBF_4$, and $LiAsF_6$, as well as corresponding salts depending on the choice of metal for the negative electrode, for example, the corresponding sodium salts. As indicated above, the electrolyte salt is optional for the battery cells of this invention, in that upon discharge of the battery, the metal sulfides or polysulfides formed can act as electrolyte salts, for example, $M_{x/z}S$ wherein x=0 to 2 and z is the valence of the metal.

As mentioned, the battery cells of this invention may include a solid-state electrolyte. An exemplary solid-state electrolyte separator is a ceramic or glass electrolyte separator which contains essentially no liquid. Specific examples of solid-state ceramic electrolyte separators include beta alumina-type materials such as sodium beta alumina, Nasicon™ or Lisicon™ glass or ceramic. Polymeric electrolytes, porous membranes, or combinations thereof are examples of a type of electrolyte separator which may include an aprotic organic liquid to produce a solid-state electrolyte separator preferably containing less than 20% liquid. Suitable polymeric electrolytes include polyethers, polyimines, polythioethers, polyphosphazenes, polymer blends, and the like and mixtures and copolymers thereof in which an appropriate electrolyte salt has optionally been added. Preferred polyethers are polyalkylene oxides, more preferably, polyethylene oxide.

In the get-state, the electrolyte separator preferably contains at least 20% (weight percentage) of an organic liquid (see the above listed liquid electrolytes for examples), with the liquid being immobilized by the inclusion of a gelling agent. Many gelling agents such as polyacrylonitrile, polyvinylidene difluoride (PVDF), or polyethylene oxide (PEO), can be used.

It should be understood that some separators employing liquid electrolytes entrained in porous polymer matrices are commonly referred to as "polymer" separator membranes. Such systems are considered liquid electrolyte systems within the context of this invention. The membrane separators employed in these systems actually serve to hold liquid electrolyte in small pores by capillary action. Essentially, a porous or microporous network provides a region for entraining liquid electrolyte. Such separators are described in U.S. Pat. No. 3,351,495 assigned to W. R. Grace & Co. and U.S. Pat. Nos. 5,460,904, 5,540,741, and 5,607,485 all assigned to Bellcore, for example. Each of these patents is incorporated herein by reference for all purposes.

The fully charged state of some cells of this invention need not require that the positive electrode be entirely converted to elemental sulfur. It may be possible in some cases to have the positive electrode be a highly oxidized form of lithium polysulfide, for example, as in $Li_2S_x$ where x is five or greater. The fully charged positive electrode may also include a mixture of such polysulfides together with elemental sulfur and possibly even some sulfide. It should be understood that during charge, the positive electrode would generally not be of uniform composition. That is, there will be some amount of sulfide, sulfur, and an assortment of polysulfides with various values of x. Also, while the electrochemically active material includes some substantial fraction of "sulfur," this does not mean that the positive electrode must rely exclusively upon sulfur for its electrochemical energy.

The electronic conductor in the positive electrode preferably forms an interconnected matrix so that there is always a clear current path from the positive current collector to any position in the electronic conductor. This provides high availability of electroactive sites and maintained accessibility to charge carriers over repeated cycling. Often such electronic conductors will be fibrous materials such as a felt or paper. Examples of suitable materials include a carbon paper from Lydall Technical Papers Corporation of Rochester, N.H. and a graphite felt available from Electrosynthesis Company of Lancaster, N.Y.

The sulfur is preferably uniformly dispersed in a composite matrix containing an electronically conductive material. Preferred weight ratios of sulfur to electronic conductor in the sulfur-based positive electrodes of this invention in a fully charged state are at most about 50:1, more preferably at most about 10:1, and most preferably at most about 5:1. The sulfur considered in these ratios includes both precipitated or solid phase sulfur as well as sulfur dissolved in the electrolyte. Preferably, the per weight ratio of electronic conductor to binder is at least about 1:1 and more preferably at least about 2:1.

The composite sulfur-based positive electrode may further optionally include performance enhancing additives such as binders, electrocatalysts (e.g., phthalocyanines, metallocenes, brilliant yellow (Reg. No. 3051-11-4 from Aldrich Catalog Handbook of Fine Chemicals; Aldrich Chemical Company, Inc., 1001 West Saint Paul Avenue, Milwaukee, Wis.) among other electrocatalysts), surfactants, dispersants (for example, to improve the homogeneity of the electrode's ingredients), and additional surface layer forming additives to protect a lithium negative electrode (e.g., organosulfur compounds, phosphates, iodides, iodine, metal sulfides, nitrides, and fluorides). Preferred binders (1) do not swell in the liquid electrolyte and (2) allow partial but not complete wetting of the sulfur by the liquid electrolyte. Examples of suitable binders include Kynar available from Elf Atochem of Philadelphia, Pa., polytetrafluoroethylene dispersions, and polyethylene oxide (of about 900 k molecular weight for example). Other additives include electroactive organodisulfide compounds employing a disulfide bond in the compound's backbone. Electrochemical energy is generated by reversibly breaking the disulfide bonds in the compound's backbone. During charge, the disulfide bonds are reformed. Examples of organodisulfide compounds suitable for use with this invention are presented in U.S. Pat. Nos. 4,833,048 and 4,917,974 issued to DeJonghe et al. and U.S. Pat. No. 5,162,175 issued to Visco et al.

The battery cells of this invention may be rechargeable "secondary" cells. Unlike primary cells which discharge only once, the secondary cells of this invention cycle between discharge and charge at least two times. Typically, secondary cells of this invention will cycle at least 50 times, with each cycle having a sulfur utilization (measured as a fraction of 1675 mAh/g sulfur output during the discharge phase of the cycle) of at least about 10%. More preferably, at least 50 cycles will have a minimum sulfur utilization of at least about 20% (most preferably at least about 30%). Alternatively, the secondary cells of this invention will cycle at least two times, with each cycle attaining at least 50% utilization of sulfur in the positive electrode.

6 EXAMPLES

The following Examples are provided to illustrate certain aspects of the present invention and to aid those of skill in the art in practicing the invention. These Examples are in no way to be considered to limit the scope of the invention in any manner.

6.1 Experiment 1: $LiAlCl_4.3SO_2$-Coated Lithium Metal Battery

An electrochemical cell was constructed containing a lithium (Li) metal anode, a porous carbon (C) cathode, and an electrolyte solution containing 0.5 moles/liter of lithium ditriflate and 3.0 moles/liter of sulfur as lithium polysulfide ($Li_2S_8$) dissolved in tetraglyme. The cell was equipped with a Li reference electrode placed between two layers of a microporous separator (sold commercially under the tradename CELGARD 2400 by Cellgard LLC of Charlotte, N.C.) Prior to insertion in the electrolyte solution, the front surface of Li electrode was coated with $LiAlCl_4.3SO_2$ at a surface density of about 2 $\mu l/cm^2$. The electrode was coated by placing the liquid $LiAlCl_4.3SO_2$ complex on the surface dropwise and then spreading the liquid over the face of the electrode using the edge of a glass plate.

The resistance at the interface between the Li electrode and the electrolyte was measured by a pulse galvanostatic method. Using short current pulses from a PAR 273 potentionstat with duration of about 1 ms, current-overpotential curves were obtained without substantially changing the properties of Li surface. The values of slopes of initial linear segments of these curves provided information about ionic resistance of the surface film on the Li electrode (see FIG. 1).

The comparison of current-voltage characteristics for Li electrode treated with $LiAlCl_4.3SO_2$ complex and without such treatment is shown on FIG. 1. According to this figure, the interface resistance of a treated Li electrode coating is about 2.7 times less than the resistance of an untreated one. Without wishing to be bound to any particular theory of action, these results are consistent with the formation of a passivating film on the surface of the lithium electrode that protects the Li metal of the electrode from reacting with the polysulfides in the electrolyte solution.

6.2 Experiment 2 The Cycling Efficiency of a Lithium Metal Battery Containing a Lithium Alloy-Forming Reagent In this experiment cells similar to the ones used in Experiment 1 were tested to obtain Li electrode cycling efficiency values. A Li electrode was prepared in the form of a thin Li foil (35–40 $\mu$m) on a Cu substrate. The Li electrode was cycled galvanostatically using a Maccor battery tester such that the charge stripped and charge plated were 1 $mAhr/cm^2$. Since the cycling process was not 100% efficient, some of the Li foil was dissolved during the Li stripping at each cycle. From the number of cycles n required to deplete the Li foil on Cu substrate the average efficiency per cycle X was calculated using the Formula (1):

$$X = \frac{Q_s - (Q_f/n)}{Q_s} \quad (1)$$

where $Q_s$ is the charge stripped (1 $mAhr/cm^2$) and $Q_f$ is the total charge of the Li foil (which was determined by completely stripping Li from Cu substrate at discharge current density of 0.5 $mA/cm^2$).

The potential of the Li electrode on the Cu substrate was continuously recorded during cycling experiment and compared against a Li reference electrode. The discharge process was interrupted when the working electrode potential exceeded 1.75 V vs. Li reference electrode. Such change in potential indicated the Li had been completely stripped from the Cu substrate.

The cycling efficiency of a Li electrode in an electrolyte solution containing 0.5 moles/liter of lithium trifluoromethansulfonimide (LiTFSI), 3.0 moles/liter of sulfur as $Li_2S_8$ in tetraglyme, and 0.05 moles/liter of $Mg(ClO_4)_2$ was determined as just described. This was compared to the cycling efficiency of a Li electrode in an electrolyte solution lacking $Mg(ClO_4)$. FIG. 2 shows galvanostatic cycling curves obtained from a Li electrode in electrolyte with and without $Mg(ClO_4)$ as an additive at discharge and charge current densities of about 0.1 mA/cm². (Note the lithium electrode potential without the additive is offset vertically (+0.1 V) to enhance legibility of the two traces. Both traces, however, are to scale.) According to this figure, Li electrode in the electrolyte with the additive delivered 43 cycles compared to 25 cycles for Li electrode in the electrolyte without this additive. Cycling efficiency values calculated using equation (1) were 82% with $Mg(ClO_4)$ vs. 68% without this additive (see Table 1).

6.3 Experiment 3. The Cycling Efficiency of a Lithium Metal Battery Containing a Lithium Alloy-Forming Reagent In this experiment a cell identical to the one used in Experiment 2, including the same additive of 0.05 moles/liter of $Mg(ClO_4)_2$, was galvanostatically cycled at discharge current density 0.5 mA/cm² and charge current density 0.1 mA/cm². As seen in FIG. 3, under such conditions Li electrode in the electrolyte with the additive delivered 52 cycles compared to 34 cycles for Li electrode in the electrolyte without this additive. (Note the lithium electrode potential without the additive is offset vertically (+0.1 V) to enhance legibility of the two traces. Both traces, however, are to scale.) This corresponds to the cycling efficiency values of 85% and 77% respectively (see Table 1).

6.4 Experiment 4: Increased Cycling Efficiency Using a Sulfide Complex-Forming Reagent In this experiment cells similar to the ones used in Experiments 2 and 3 were used, but the additive included was 0.1 moles/liter of $Ba(ClO_4)_2$. The cells were galvanostatically cycled at discharge current densities 0.1 and 0.5 mA/cm² and charge current density 0.1 mA/cm². Under such conditions, the measured Li cycling efficiency values in cells containing $Ba(ClO_4)_2$ were significantly higher than in cells without this additive: 90% at discharge rate of 0.5 mA/cm² and 76% at 0.1 mA/cm² (see Table 1).

TABLE 1

| Solution | Discharge/charge Rate (mA/cm²) | Avg. Cycling Efficiency (%) |
|---|---|---|
| 3 M S as $Li_2S_8$ 0.5 M LiDTF, Tetraglyme | 0.1/0.1 | 68% |
|  | 0.5/0.1 | 77% |
| Same + 0.05 M $Mg(ClO_4)_2$ | 0.1/0.1 | 82% |
|  | 0.5/0.1 | 85% |
| Same + 0.1 M $Ba(ClO_4)_2$ | 0.1/0.1 | 76% |
|  | 0.5/0.1 | 90% |

7 BIBLIOGRAPHY

The following references are incorporated herein by reference in their entirety and for all purposes.

Dahn, J. R., et al. (1998). 9th International Meeting on Lithium Batteries, Edinburgh, Scotland.

De Gott, P. (1986). *Polymere Carbone-Soufre Synthese et Proprietes Electrochimiques*, Institute National Polytechnique de Grenoble.

Dey, A. N., et al. (1989). "Inorganic Electrolyte Li/CuCl2 Rechargeable Cell." *J. Electrochem. Soc.* 136(6): 1618–1621.

Dunger, H.-J., H. G., et al. (1993). "Lithium-cycling Efficiency in Inorganic Electrolyte Solution." *J. Power Sources* 43–44: 405–408.

Foster, D. L., et al. (1988). "New Highly Conductive Inorganic Electrolytes. The Liquid SO2 Solvates at the Alkali and Alkaline Earth metal Tetrachloroaluminates." *J. Electrochem. Soc.* 135(11): 2682–2686.

Idota, Y., et al. (1997). Nonaqueous Secondary Battery. U.S. Pat. No. 5,618,640.

Rauh, et al. (1979). "A Lithium/Dissolved Sulfur Battery with an Organic Electrode." *J. Electrochem. Soc.* 126(4): 523.

Rauh, et al. (1989). "Rechargable Lithium-Sulfur Battery." *J. Power Sources* 26: 269.

Thackeray (1998). 9th International Meeting on Lithium Batteries, Edinburgh, Scotland.

What is claimed:

1. An electrochemical cell, comprising a lithium electrode and a sulfur electrode including at least one of elemental sulfur, lithium sulfide, and a lithium polysulfide, said lithium electrode having a lithium metal electrode surface including a surface coating that is effective to increase the cycling efficiency of said electrochemical cell.

2. The electrochemical cell of claim 1, wherein said lithium electrode is in an electrolyte solution.

3. The electrochemical cell of claim 2, wherein said electrolyte solution contains at least one of elemental sulfur, a sulfide, and a polysulfide.

4. The electrochemical cell of claim 3, wherein said surface coating of said lithium electrode is formed prior to contacting said lithium electrode with said electrolyte.

5. The electrochemical cell of claim 4, wherein said surface coating is formed by contacting said surface of said lithium electrode with $LiAlCl_4.3SO_4$.

6. The electrochemical cell of claim 5, wherein said surface coating comprises a reaction product of lithium metal and $LiAlCl_4.3SO_4$.

7. The electrochemical cell of claim 6, wherein said surface coating comprises $Li_2S_2O_4$.

8. The electrochemical cell of claim 3, wherein said surface coating of said lithium electrode is formed after contacting said lithium electrode with said electrolyte.

9. The electrochemical cell of claim 8, wherein said surface coating of said lithium electrode is formed by the reaction of a chemical species in said electrolyte that is effective to form an alloy with lithium metal.

10. The electrochemical cell of claim 9, wherein said chemical species includes a mutivalent transition- or alkaline earth metal.

11. The electrochemical cell of claim 10, wherein said multivalent metal is a salt of a metal selected from the group consisting of Mg, Al, Bi, Sn, Pb, Cd, Si, In, and Ga, said salt being soluble in said electrolyte.

12. An electrochemical cell, comprising an electrode and an electrolyte containing one or more sulfur compounds including at least one of elemental sulfur, sulfides, and polysulfides, said electrolyte including a reagent that is effective to form a substantially insoluble metal-sulfide complex in said electrolyte to increase thereby the cycling efficiency of said electrode.

13. The electrochemical cell of claim 12, wherein said electrode is a lithium electrode.

14. The electrochemical cell of claim 13, wherein said lithium electrode is combined with a sulfur-containing electrode.

15. The electrochemical cell of claim 14, wherein said reagent is a salt of Ba or Mo.

16. The electrochemical cell of claim 15, wherein said reagent is a salt of Ba.

17. The electrochemical cell of claim 14, wherein said sulfur-containing electrode includes at least one of elemental sulfur, sulfides, and polysulfides.

18. The electrochemical cell of claim 17, wherein said active sulfur-containing electrode further includes an ionically conductive material.

19. The electrochemical cell of claim 18, wherein said ionically conductive material is a polyalkyleneoxide.

20. An electrochemical cell, comprising a lithium-tin alloy, the surface of said electrode including a lithium oxide coating, and a sulfur electrode including at least one of elemental sulfur, a lithium sulfide, or a lithium polysulfide.

21. The electrochemical cell of claim 20, wherein said electrolyte includes at least one of elemental sulfur, a sulfide, or a polysulfide.

22. A battery cell comprising:
   a. a positive electrode comprising a mixture of
      i. an electrochemically active material, and
      ii. an electronically conductive material,
   b. a negative electrode comprising a lithium metal electrode surface including a surface coating that is effective to increase the cycling efficiency of said electrochemical cell; and
   c. an electrolyte electronically separating the positive and negative electrodes;
      wherein said electrochemically active material includes at least one component selected from the group consisting of elemental sulfur, sulfides of lithium, polysulfides of lithium, and combinations thereof.

23. The battery cell of claim 22, wherein said surface coating is formed by contacting said surface of said lithium electrode with $LiAlCl_4 \cdot 3SO_4$.

24. The battery cell of claim 23, wherein said surface coating comprises a reaction product of lithium metal and $LiAlCl_4 \cdot 3SO_4$.

25. The battery cell of claim 24, wherein said surface coating comprises $Li_2S_2O_4$.

26. A battery cell comprising:
   a. a positive electrode comprising a mixture of
      i. an electrochemically active material, and
      ii. an electronically conductive material,
   b. a negative electrode comprising a lithium-tin alloy and lithium oxide composite;
   c. an electrolyte electronically separating the positive and negative electrodes;
      wherein said electrochemically active material includes at least one component selected from the group consisting of elemental sulfur, sulfides of lithium, polysulfides of lithium, and combinations thereof.

* * * * *

UNITED STATES PATENT AND TRADEMARK OFFICE
CERTIFICATE OF CORRECTION

PATENT NO. : 6,017,651
DATED : January 25, 2000
INVENTOR(S) : Yevgeniy S. Nimon, May-Ying Chu, and Steven J. Visco It is certified that error appears in the above-identified patent and that said Letters Patent is hereby corrected as shown below:

Column 2 line 43, please replace "$LiAlCl_4.3SO_4$" with --$LiAlCl_2.3SO_2$--.

Column 2 line 45, please replace "$LiAlCl_4.3SO_4$" with --$LiAlCl_2.3SO_2$--.

Column 14 line 30, please replace "$LiAlCl_4.3SO_4$" with --$LiAlCl_2.3SO_2$--.

Column 14 line 33, please replace "$LiAlCl_4.3SO_4$" with --$LiAlCl_2.3SO_2$--.

Column 16 line 5, please replace "$LiAlCl_4.3SO_4$" with --$LiAlCl_2.3SO_2$--.

Column 16 line 8, please replace "$LiAlCl_4.3SO_4$" with --$LiAlCl_2.3SO_2$--.

Signed and Sealed this

Second Day of January, 2001

Attest:

Attesting Officer

Q. TODD DICKINSON

Commissioner of Patents and Trademarks